(12) United States Patent
Tanaka et al.

(10) Patent No.: US 10,412,963 B2
(45) Date of Patent: Sep. 17, 2019

(54) AGRICULTURAL AND HORTICULTURAL FUNGICIDE COMPOSITION AND PLANT DISEASE CONTROLLING METHOD

(71) Applicant: SDS BIOTECH K.K., Tokyo (JP)

(72) Inventors: Keijitsu Tanaka, Tsukuba (JP); Mutsumi Miyazaki, Tsukuba (JP); Yusuke Amaki, Tsukuba (JP)

(73) Assignee: SDS BIOTECH K.K., Tokyo (JP)

( * ) Notice: Subject to any disclaimer, the term of this patent is extended or adjusted under 35 U.S.C. 154(b) by 0 days.

(21) Appl. No.: 16/095,133

(22) PCT Filed: Aug. 9, 2016

(86) PCT No.: PCT/JP2016/073402
§ 371 (c)(1),
(2) Date: Oct. 19, 2018

(87) PCT Pub. No.: WO2018/029775
PCT Pub. Date: Feb. 15, 2018

(65) Prior Publication Data
US 2019/0124923 A1    May 2, 2019

(51) Int. Cl.
*A01N 43/16* (2006.01)
*A01N 63/02* (2006.01)
*A01N 59/08* (2006.01)

(52) U.S. Cl.
CPC ............. *A01N 43/16* (2013.01); *A01N 63/02* (2013.01); *A01N 59/08* (2013.01)

(58) Field of Classification Search
None
See application file for complete search history.

(56) References Cited

U.S. PATENT DOCUMENTS

| | | |
|---|---|---|
| 2012/0302494 A1 | 11/2012 | Guilhabert-Goya et al. |
| 2013/0331311 A1 | 12/2013 | Guilhabert-Goya et al. |

FOREIGN PATENT DOCUMENTS

| | | | |
|---|---|---|---|
| JP | 57-008718 | A | 1/1982 |
| JP | 59-212416 | A | 12/1984 |
| JP | 01-175910 | A | 7/1989 |
| JP | 06-135811 | A | 5/1994 |
| JP | 2673718 | B2 | 11/1997 |
| JP | 2014-518878 | A | 8/2014 |
| WO | 2007/040131 | A1 | 4/2007 |
| WO | 2013/094055 | A1 | 6/2013 |

OTHER PUBLICATIONS

Kei Arima et al., "Surfactin, a Crystalline Peptidelipid Surfactant Produced by Bacillus Subtilis : Isolation, Characterization AMD Its Inhibition of Fibrin Clot Formation", Biochemical and Biophysical Research Communications, 1968, pp. 488-494, 7 pages, vol. 31, No. 3.
Jean-Marc Bonmatin et al., "Production, isolation and characterization of [Leu4]- and [Ile4]surfactins from Bacillus subtilis", Letter in Peptide Science, 1995, pp. 41-47, 7 pages, vol. 2.
Soumitra Paul Chowdhury et al., "Biocontrol mechanism by root-associated Bacillus amyloliquefaciens FZB42—a review", Frontiers in Microbiology, Jul. 28, 2015, pp. 1-11, 11 pages, vol. 6.
Isabelle Grangemard et al., "Lichenysins G, a Novel Family of Lipopeptide Biosurfactants from Bacillus licheniformis IM 1307: Productions, Isolation and Structural Evaluation by NMR and Mass Spectrometry", The Journal of Antibiotics, Apr. 1999, pp. 363-373, 9 pages, vol. 52, No. 4.
Masa Hamada et al., "Prumycin Produced by Bacillus Cereus", The Journal of Antibiotics, Jan. 1983, p. 36, 1 page, vol. 86.
Akira Hasegawa et al., "Synthesis of 2,4-Diamino-2,4-dideoxy-L-arabinose Derivatives (Prumycin Derivatives)", Agric. Biol. Chem., 1978, pp. 153-158, 6 pages, vol. 42, No. 1.
Akira Hasegawa et al., "A new synthesis of Prumycin", Carbohydrate Research, 1976, pp. 10-12, 3 pages, vol. 51.
Akira Hasegawa et al., "Synthesis of Prumycin and Related Compounds", Carbohydrate Research, 1976, pp. 137-149, 13 pages, vol. 52.
Hironobu Hashimoto et al., "A Synthesis of Prumycin", Carbohydrates Research, 1978, pp. 75-84, 10 pages, vol. 60.
Hironobu Hashimoto et al., "Synthesis of L-xylo and L-ribo analogues of prumycin", Carbohydrate Research, 1979,pp. 261-266, 6 pages, vol. 72.
Jun Iwabuchi et al., "A Facile Synthesis of Prumycin", J. Carbohydrate Chemistry, 1988, pp. 605-616, 12 pages, vol. 7, No. 3.
Katharina Jenny et al., "Biosurfactants from Bacillus licheniformis: structural analysis and characterization", Applied Microbiology and Biotechnology, 1991, pp. 5-13, 9 pages, vol. 36.
Toju Hata et al., "A New Antifungal Antibiotic, Prumycin", The Journal of Antibiotics, Dec. 1971, pp. 900-901, 2 pages, vol. 24, No. 12.
A. Kakinuma et al., "Determination of Amino Acid Sequence in Surfactin, a Crystalline Peptidelipid Surfacntant Produced by Bacillus subtilis", Agr. Biol. Chem., 1969, pp. 971-972, 2 pages, vol. 33, No. 6.
Hassan Akhtar Khan et al., "Synthesis of 4-(D-Alanylamino)-2-amino-2,4-dideoxy-D-xylose", Bulletin of the Chemical Society of Japan, 1978, pp. 951-952, 2 pages, vol. 51, No. 3.
Hiroyoshi Kuzuhara et al., "Synthesis of Prumycin", Tetrahedron Letters, 1975, pp. 1853-1856, 4 pages, vol. 16, No. 22/23.
Hiroyoshi Kuzuhara et al., Synthesis of a Hexose-Analogue of Prumycin (4-D-Alanylamino-2-Amino-2,4-Dideoxy-D-Galactopyranose), Tetrahedron Letters, 1976, pp. 379-382, 4 pages, vol. 17, No. 5.

(Continued)

*Primary Examiner* — Alton N Pryor
(74) *Attorney, Agent, or Firm* — Sughrue Mion, PLLC

(57) ABSTRACT

An agricultural and horticultural fungicide composition including prumycin and a surfactin family member as active components and a plant disease controlling method. As the surfactin, family member, surfactin and [Ile$^7$]surfactin are preferred. The composition preferably further contains calcium chloride comprises for improving storage stability.

6 Claims, No Drawings

(56) References Cited

OTHER PUBLICATIONS

Satoshi Omura et al., "Production and Isolation of a New Antifungal Antibiotic, Prumycin and Taxonomic Studies of *Streptomyces* sp., Strain No. F-1028", Agr. Biol. Chem., 1973, pp. 2805-2812, 8 pages, vol. 37, No. 12.

Satoshi Omura et al., "Structure of Prumycin", J. Chem. Soc. Perkin Trans, 1974, pp. 1627-1631, 5 pages, vol. 1.

Francoise Peypoux et al., "Isolation and characterization of a new variant of surfactin, the [Val7]surfactin", Eur. J. Biochem., 1991, pp. 101-106, 6 pages, vol. 202.

Francoise Peypoux et al., "[Ala4]Surfactin, a novel isoform from Bacillus subtilis studied by mass and NMR spectroscopies", Eur. J. Biochem., 1994, pp. 89-96, 8 pages, vol. 224.

Jos M. Raaijmakers et al., "Natural functions of lipopeptides from Bacillus and Pseudomonas: more than surfactants and antibiotics", FEMS Microbiol Rev, 2010, pp. 1037-1062, 26 pages, vol. 34.

Keijitsu Tanaka et al., "Synergistic Effects of [Ile7]Surfactin Homologues with Bacillomycin D in Suppression of Gray Mold Disease by Bacillus amyloliquefaciens Biocontrol Strain SD-32", Journal of Agricultural and Food Chemistry, 2015, pp. 5344-5574, 10 pages, vol. 63.

Jacqueline A. Trischman et al., "Halobacillin: a Cytotoxic Cyclic Acylpeptide of the Iturin Class Produced by a Marine Bacillus", Tetrahedron Letters, 1994, pp. 5571-5574, 4 pages, vol. 35, No. 31.

Michail M. Yakimov et al., "Structural characterization of lichenysin A components by fast atom bombardment tandem mass spectrometry", Biochimica et Biophysica Acta, 1999, pp. 273-280, 8 pages, vol. 1438.

Juji Yoshimura et al., "A New Synthesis of Prumycin", Chemistry Letters, 1976, pp. 201-202, 2 pages, vol. 5.

International Search Report for PCT/JP2016/073402 dated Oct. 18, 2016.

Decision to Grant JP 2017-561020 dated Dec. 27, 2017.

AGRICULTURAL AND HORTICULTURAL FUNGICIDE COMPOSITION AND PLANT DISEASE CONTROLLING METHOD

CROSS REFERENCE TO RELATED APPLICATIONS

This application is a National Stage of International Application No. PCT/JP2016/073402 filed Aug. 9, 2016.

TECHNICAL FIELD

The present invention relates to an agricultural and horticultural fungicide composition and a plant disease controlling method.

BACKGROUND ART

Hitherto, many agricultural and horticultural fungicides have been known. However, owing to problems with an effect, chemical resistance, safety, and the like, there is a need for a more effective chemical that can be more safely used.

Prumycin (4-N-D-alanyl-2,4-diamino-2,4-dideoxyarabinose) is known as a chemical having effects against gray mold, sclerotial disease, powdery mildew, and the like. Prumycin was isolated from a culture filtrate of a *Streptomyces* sp. strain F-1028 by Hata et al. in 1971 (Non Patent Literature 1), and later, in 1973, it was reported by Omura et al. that effects of prumycin were found against gray mold and sclerotial disease of beans, and cucumber powdery mildew (Non Patent Literature 2). The structure of prumycin was determined by Omura et al. in 1974 (Non Patent Literature 3). After that, three independent groups achieved total synthesis (Non Patent Literatures 4 to 13), and a structure represented by the following formula was identified.

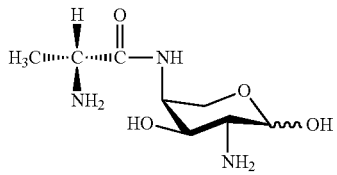

With regard to naturally occurring prumycin, it was revealed that, besides the above-mentioned *Streptomyces* sp., a specific strain of *Bacillus cereus* produced prumycin (Patent Literature 1 and Non Patent Literature 14). Further, in 1989, it was reported that a specific strain of *Bacillus subtilis* produced prumycin (Patent Literature 2).

However, although its fundamental activity is high, prumycin has not yet been put into practical use owing to lack of effect in actual use. In order to solve the problem of lack of effect, its combined use with another chemical, that is, an iturin A-based peptide (Patent Literature 3) or benomyl (Patent Literature 4) has been considered, but all the same, has not yet been put into practical use owing to lack of effect.

Meanwhile, surfactin family members are also substances that have long been known. In 1968, K. Arima et al. isolated a substance having a high surface-active ability from a culture broth of *B. subtilis*, and named the substance surfactin (Non Patent Literature 15). The structure of surfactin was elucidated by A. Kakinuma et al. in 1969, and revealed to be, as shown in Table 1, a lipodepsipeptide structure formed of: a C13 to 17 β-hydroxy fatty acid whose terminal branching structure has any of iso, anteiso (hereinafter abbreviated as ai), and normal (hereinafter abbreviated as n) side-chain structures; and four molecules of Leu, and one molecule each of Val, Glu, and Asp (Non Patent Literature 16).

After that, as surfactin family members, [Ala⁴]surfactin (Non Patent Literature 17), [Leu⁴]surfactin (Non Patent Literature 18), [Ile⁴]surfactin (Non Patent Literature 18), and [Val⁷]surfactin (Non Patent Literature 19) were each isolated from a culture broth of *B. subtilis* and structurally determined. Further, [Ile⁷]surfactin (Non Patent Literatures 20 and 21) was isolated from a culture broth of each of *B. licheniformis* and *B. amyloliquefaciens* and structurally determined, and halobacillin (Non Patent Literature 22) and lichenysins A and G (Non Patent Literatures 23 and 24) were isolated from *Bacillus* sp. bacteria including *B. licheniformis* and structurally determined (Table 1).

TABLE 1

β-OH fatty acid→1→2→3
↑         ↓
7←6←5←4

| | α-amino acids | | | | | | β-OH-fatty acid (carbon number and |
|---|---|---|---|---|---|---|---|
| | 1 | 2 | 3 | 4 | 5 | 6 | 7 structure) |
| Surfactin | Glu | Leu | Leu | Val | Asp | Leu | Leu ai-$C_{13}$, iso-$C_{13}$, n-$C_{13}$, iso-$C_{14}$, n-$C_{14}$, ai-$C_{15}$, iso-$C_{15}$, n-$C_{15}$, iso-$C_{16}$, ai-$C_{17}$ |
| [Ala⁴] Surfactin | Glu | Leu | Leu | Ala | Asp | Leu | Leu iso-$C_{14}$, n-$C_{14}$, ai-$C_{15}$, iso-$C_{15}$, n-$C_{15}$ |
| [Leu⁴] Surfactin | Glu | Leu | Leu | Leu | Asp | Leu | Leu — |
| [Ile⁴] Surfactin | Glu | Leu | Leu | Ile | Asp | Leu | Leu — |
| [Val⁷] Surfactin | Glu | Leu | Leu | Val | Asp | Leu | Val ai-$C_{13}$, iso-$C_{14}$, n-$C_{14}$, ai-$C_{15}$ |
| [Ile⁷] Surfactin | Glu | Leu | Leu | Val | Asp | Leu | Ile ai-$C_{13}$, iso-$C_{13}$, iso-$C_{14}$, n-$C_{14}$, ai-$C_{15}$, iso-$C_{15}$ |
| Halobacillin (lichenysins) | Gln | Leu | Leu | Val | Asp | Leu | Ile — |

Underlined amino acids represent D-enantiomers.

The surfactin family members were originally isolated as substances each having a potent surface-active ability. However, research in recent years has revealed that the surfactin family members play important roles in biocontrol activity of the *Bacillus* sp. bacteria (e.g., involvement in bacterial colonization of a plant and induction of resistance in a plant) (Non Patent Literatures 25 and 26). However, no report has heretofore been made of an interaction (synergistic effect) between prumycin and a surfactin family member.

CITATION LIST

Patent Literature

[PTL 1] JP 57-8718 B2
[PTL 2] JP 2673718 B2

[PTL 3] JP 59-212416 A
[PTL 4] JP 01-175910 A

Non Patent Literature

[NPL 1] J. Antibiot., 24, 900-901 (1971)
[NPL 2] Agrc. Biol. Chem., 37, 2805-2812 (1973)
[NPL 3] J. Chem. Soc. Perkin Trans, 1, 1627-1631 (1974)
[NPL 4] Tetrahedron Lett., 16, 1853-1856 (1975)
[NPL 5] Tetrahedron Lett., 17, 379-382 (1976)
[NPL 6] Chem. Lett., 5, 201-202 (1976)
[NPL 7] Carbohyd. Res., 60, 75-84 (1978)
[NPL 8] Carbohyd. Res., 72, 261-266 (1979)
[NPL 9] B. Chem. Soc. Jpn., 51, 951-952 (1978)
[NPL 10] Carbohyd. Res., 51, 10-12 (1976)
[NPL 11] Agric. Biol. Chem., 42, 153-158 (1978)
[NPL 12] Carbohyd. Res., 52, 137-149 (1976)
[NPL 13] J. Carbohyd. Chem., 7, 605-616 (1988)
[NPL 14] J. Antibiot., 36, 86, (1983)
[NPL 15] Biochem. Biophys. Res. Commun., 31, 488-494 (1968)
[NPL 16] Agric. Biol. Chem., 33, 971-972 (1969)
[NPL 17] Eur. J. Biochem., 224, 89-96 (1994)
[NPL 18] Lett. Pept. Sci., 2, 41-47 (1995)
[NPL 19] EUR. J. Biochem., 202, 101-106 (1991)
[NPL 20] Appl. Microbiol. Biotechnol., 36, 5-13 (1991)
[NPL 21] J. Agric. Food Chem., 63, 5344-5353 (2015)
[NPL 22] Tetrahedron Lett., 35, 5571-5574 (1994)
[NPL 23] Biochim. Biophys. Acta, Mol. Cell Biol. Lipids, 1438, 273-280 (1999)
[NPL 24] J. Antibiot., 52, 363-373 (1999)
[NPL 25] FEMS Microbiol. Rev., 34, 1037-1062 (2010)
[NPL 26] Frontiers in Microbiol., 6, 1-11 (2015)

SUMMARY OF INVENTION

Technical Problem

It is an object of the present invention to provide a novel agricultural and horticultural fungicide composition and plant disease controlling method each using prumycin and surfactin family member.

Solution to Problem

The inventors of the present invention have investigated the effects of relate-art fungicidal compounds in detail, and have found that: (1) a surfactin family member markedly enhances the effect of prumycin to exhibit extremely useful fungicide activity; and (2) the addition of calcium chloride to the surfactin family member and prumycin markedly improves the storage stability thereof. Thus, the inventors have completed the present invention, which is directed to a novel agricultural and horticultural fungicide composition containing prumycin and a surfactin family member as active components, and further containing calcium chloride.

That is, the present invention provides the following agricultural and horticultural fungicide composition and plant disease controlling method.
1. An agricultural and horticultural fungicide composition, including prumycin and a surfactin family member as active components.
2. The agricultural and horticultural fungicide composition according to the above-mentioned item 1, in which the surfactin family member includes surfactin and/or [Ile$^7$] surfactin.
3. The agricultural and horticultural fungicide composition according to the above-mentioned item 1 or 2, further including 0.1 mass % to 10 mass % of calcium chloride.
4. A plant disease controlling method, including applying to a plant the agricultural and horticultural fungicide composition of any one of the above-mentioned items 1 to 3.
5. The plant disease controlling method according to the above-mentioned item 4, in which a concentration of prumycin in a liquid to be applied at a time of the applying to a plant is 0.5 ppm or more.
6. The plant disease controlling method according to the above-mentioned item 4 or 5, in which a concentration of the surfactin family member in a liquid to be applied at a time of the applying to a plant is 1 ppm or more.

Advantageous Effects of Invention

The agricultural and horticultural fungicide composition of the present invention can be used as a safe agricultural and horticultural fungicide composition having excellent fungicide activity.

DESCRIPTION OF EMBODIMENTS

Prumycin (4-N-D-alanyl-2,4-diamino-2,4-dideoxyarabinose) to be used in the present invention may be produced through chemical synthesis by the method of any of Non Patent Literatures 4 to 13. In addition, prumycin may be produced by being biosynthesized as a fermentation product of a microorganism having an ability to produce prumycin, such as a *Streptomyces* sp., *Bacillus cereus*, or *Bacillus subtilis*, and then being purified from a culture filtrate thereof.

A salt of prumycin is not particularly limited, and examples thereof include a hydrochloride, a phosphate, a borate, a formate, an acetate, and a benzoate. Of those, a hydrochloride and an acetate are preferred.

A surfactin family member to be used in the present invention is a compound disclosed in any of Non Patent Literatures 15 to 26, preferably surfactin or [Ile$^7$]surfactin. Each of those surfactin family members has homologues containing C13 to C17 β-hydroxy fatty acids shown in Table 1. The surfactin family member may be produced by being chemically synthesized, and by being biosynthesized as a fermentation product of a microorganism having an ability to produce the surfactin family member, and then purified from a culture filtrate thereof. An example of such microorganism is a *Bacillus* sp. strain AT-332. In addition, a commercially available surfactin family member may also be used.

The *Bacillus* sp. strain AT-332 has been deposited at the following depository as *Bacillus* sp. AT-332: NITE Patent Microorganisms Depositary (2-5-8 Kazusakamatari, Kisarazu-shi, Chiba 292-0818, Japan) (date of the original deposit (accession date): May 2, 2011, accession number: NITE BP-1095).

A salt of the surfactin family member is not particularly limited, and examples thereof include a sodium salt, a potassium salt, a calcium salt, and an ammonium salt. Of those, a sodium salt is preferred.

As a culture method for each of the microorganisms having abilities to produce prumycin and surfactin, the microorganisms may each be grown by known means, such as static culture on a solid medium, or liquid culture. The kind of medium, culture conditions, and the like that may be utilized are not particularly limited as long as those bacteria survive and grow. Examples of the medium include: general media, such as a meat extract medium; and a medium containing glucose, peptone, and a yeast extract. In addition, other than liquid media, solid media, such as a slant medium and a plate medium each containing agar, may be used.

As a carbon source of the medium, any material that the above-mentioned bacterial strain can utilize may be utilized. Specific examples thereof include: saccharides, such as glucose, galactose, lactose, sucrose, maltose, a malt extract, molasses, starch syrup, and starch hydrolysate; and other various synthetic or natural carbon sources that the microorganisms having abilities to produce prumycin and surfactin family member can utilize.

Similarly, as a nitrogen source of the medium, various synthetic or natural products that the bacterial strain can utilize, including organic nitrogen-containing products, such as peptone, a meat extract, a yeast extract, soybean flour, and corn steep liquor, may be utilized.

In addition, in accordance with a conventional method of culturing microorganisms, inorganic salts, such as sodium chloride and phosphates, salts of metals, such as calcium, magnesium, and iron, and sources for micronutrients, such as vitamins and amino acids, may also be added as required.

The culture may be performed under an aerobic condition, such as in shaking culture or aeration culture. A culture temperature is from 20° C. to 40° C., preferably from 25° C. to 35° C., a pH is from 5 to 8, preferably from 6 to 7, and a culture period is from 1 day to 4 days, preferably from 2 days to 3 days.

A method for the purification of each of prumycin and the surfactin family member from culture broth is not particularly limited, but the purification may be performed by a known method, such as acid precipitation, salting out, ultrafiltration, any of various kinds of chromatography, or electrophoresis.

The content of each of prumycin and the surfactin family member in the agricultural and horticultural fungicide composition of the present invention depends on a form of use and a dilution factor, and is not particularly limited. However, it is preferred that the concentration of prumycin in a liquid to be spread at the time of application to a plant be 0.5 ppm or more. In addition, it is preferred that the concentration of the surfactin family member at the time of application to a plant be 1 ppm or more.

When calcium chloride is added to the agricultural and horticultural fungicide composition of the present invention containing prumycin and the surfactin family member, its storage stability is markedly improved.

The content of calcium chloride depends on a form of use and a dilution factor, and is not particularly limited, but is from 0.1 mass % to 10 mass %, preferably from 1 mass % to 5 mass % with respect to the agricultural and horticultural fungicide composition.

The agricultural and horticultural fungicide composition of the present invention has higher fungicide activity than a composition using only prumycin as its active component. Therefore, the agricultural and horticultural fungicide composition of the present invention is useful for plant disease control, and various plant diseases can be prevented by allowing the agricultural and horticultural fungicide composition of the present invention itself or a dilute solution thereof to be present on a plant body, such as a root, a stem, a leaf, or a seed, or in a cultivation soil therefor.

The agricultural and horticultural fungicide composition of the present invention can control plant diseases resulting from fungi and bacteria belonging to Oomycetes, Ascomycetes, Basidiomycetes, and Deuteromycetes depending on its application form.

Specific examples of the fungi and bacteria causing the diseases that can be controlled by the agricultural and horticultural fungicide composition of the present invention include, but not limited to: *Pyricularia oryzae, Cochliobolus miyabeanus, Rhizoctonia solani*, and *Gibberella fujikuroi* for rice; *Erysiphe graminis* f.sp. *hordei, Erysiphe graminis* f.sp. *tritici, Puccinia striiformis, Puccinia graminis, Puccinia recondita* f.sp. *tritici, Puccinia hordei, Gibberella zeae, Pyrenophora teres, Typhula incarnata, Typhula ishikariensis, Sclerotinia borealis, Micronectriella nivalis, Ustilago nuda, Tilletia caries, Tilletia foetida, Tapesia yallundae, Phynchosporium secalis* f.sp. *hordei, Septoria tritici*, and *Leptosphaeria nodorum* for winter cereals; *Diaporthe citri, Elsinoe fawcettii, Phytophthora citrophthora, Penicillium digitatum*, and *Penicillium italicum* for citrus; *Monilinia mali, Valsa ceratosperma, Podosphaera leucotricha*, and *Alternaria alternata* apple pathotype, *Venturia inaequalis, Gymnosporangium yamadae, Botryophaeria berengeriana* f.sp. *piricola, Zygophiala jamaicensis, Gloeodes pomigena, Mycosphaerella pomi, Glomerella cingulata*, and *Diplocarpon mali* for apple; *Venturia nashicola, Alternaria alternata* japanese pear pathotype, *Physalospora piricola*, and *Gymnosporangium asaticum* for pear; *Monilinia fructicola, Cladosporium carpophilum*, and *Phomopsis* sp. for peach; *Pseudocercospora vitis, Marssonina viticola, Elsinoe ampelina, Glomerella cingulata, Uncinula necator, Phakopsora ampelopsidis*, and *Phomopsis* sp. for grape; *Phyllactinia kakicola, Colletotrichum gloeosporioides, Cercospora kaki*, and *Mycosphaerella nawae* for Japanese persimmon; *Cladosporium carpophilum* for Japanese apricot; *Monilinia fructicola* for cherry; *Sphaerotheca fuliginea, Didymella bryoniae*, and *Colletotrichum acutatum* for gourds; *Alternaria solani* and *Cladosporium fulvum* for tomato; *Phomopsis vexans* and *Erysiphe cichoracearum* for eggplant; *Alternaria japonica, Alternaria bracicae, Alternaria brassicicola*, and *Cercosporella brassicae* for brassica vegetables; *Puccinia allii* for green onion; *Pythium ultimum* and *Pythium zingiberis* for ginger; *Sphaerotheca humuli* and *Glomerella cingulata* for strawberry; *Cercospora kikuchii, Elsinoe glycines*, and *Diaporthe phaseolorum* var. *sojae* for soybeans; *Cercospora canescens* and *Uromyces phaseoli* var. *azukicola* for azuki beans; *Colletotrichum lindemuthianum* for kidney beans; *Cercosporidium personatum, Cercospora arachidicola*, and *Sphaceloma arachidis* for peanuts; *Erysiphe pisi* for peas; *Alternaria solani* for potato; *Exobasidium reticulatum, Elsinoe leucospila, Pestalotiopsis theae*, and *Pestalotiopsis longiseta* for tea; *Alternaria longipes, Erysiphe cichoracearum*, and *Colletotrichum gloeosporioides* for tobacco; *Cercospora beticola* for sugar beet; *Curvularia geniculata* and *Ceratobasidium* spp. for lawn grass; *Diplocarpon rosae* and *Shaerotheca pannosa* for rose; *Septoria obesa* and *Puccinia horiana* for chrysanthemum; *Rhizoctonia solani* causing large patch disease, *Rhizoctonia solani* causing brown patch disease, *Pythium aphanidermatum, Pythium periplocum, Sclerotinia homoeocarpa, Gaeumannomyces graminis* var. *graminis, Ophiosphaerella korrae* causing necrotic ring spot disease, *Gaeumannomyces graminis* var. *avenae, Ophiosphaerella korrae* causing spring dead spot disease, *Magnaporthe poae, Lycoperdon perlatum, Trechispora cohaerens* causing white patch disease, *Trechispora cohaerens* causing white bright disease, *Typhula incarnata, Puccinia zoysiae, Waitea circinata* var. *circinata, Ceratobasidium graminuem, Colletotrichum graminicola, Fusarium oxysporum*, and *Magnaporthe grisea* for lawn grass; and *Botrytis cinerea* and *Sclerotinia sclerotiorum* for various crops.

In addition, the application amount of the agricultural and horticultural fungicide composition of the present invention may be determined as appropriate for the above-mentioned pathogenic microbes and crops.

The agricultural and horticultural fungicide composition of the present invention may be directly used, and may also be used as a chemical suitable for an agricultural and horticultural fungicide, such as a granule, a powder and granule, a fine granule, a liquid formulation, a water soluble powder, an oil solution, an emulsifiable concentrate, a surf formulation, an emulsion, a microemulsion, a suspoemulsion formulation, an emulsion oil in water (EW) formulation, a microcapsule, a wettable powder, a suspension, a flowable, a tablet, a water dispersible granule, a dry flowable, an aerosol, a paste, a cyclodextrin formulation, a jumbo-pellet, a pack, a water soluble bag, a dust formulation, a smoking formulation, or a fumigant. The agricultural and horticultural fungicide composition of the present invention may be used as a chemical obtained by diluting the composition with an inert liquid or solid carrier, and as required, adding a surfactant, a dispersant, or any other auxiliary substance. Specific formulation examples include formulation forms such as a granule, a dust formulation, a wettable powder, a water dispersible granule, a suspension formulation, and an emulsifiable concentrate.

As required, the agricultural and horticultural fungicide composition according to the present invention may contain an additive that is generally used for an agricultural chemical formulation. Examples of the additive include a carrier, such as a solid carrier or a liquid carrier, a surfactant, a binder, a tackifier, a thickener, a colorant, an extender, an antifreezing agent, a caking inhibitor, a disintegrant, a stabilizing agent, and an antiseptic agent, and in addition, an antiseptic agent, a plant piece, or the like may be used as an addition component as required. Those additives may be used alone or in combination thereof.

The above-mentioned addition components are described. Examples of the solid carrier include: natural minerals, such as quartz, clay, kaolinite, pyrophyllite, sericite, talc, chalk, bentonite, attapulgite, montmorillonite, acid clay, zeolite, natural rock, diatomaceous earth, calcite, marble, floatstone, meerschaum, and dolomite; inorganic salts, such as calcium carbonate, ammonium sulfate or other ammonium salts, sodium sulfate, and potassium chloride; organic solid carriers, such as starch, cellulose, and plant powder; plastic carriers, such as polyethylene, polypropylene, and polyvinylidene chloride; and synthetic silicic acid, synthetic silicates, alumina, pulverized silica, and silicates. Those solid carriers may be used alone or in combination thereof.

Examples of the liquid carrier may include: alcohols, which are roughly classified into monohydric alcohols, such as methanol, ethanol, propanol, isopropanol, and butanol, and polyhydric alcohols, such as ethylene glycol, diethylene glycol, propylene glycol, hexylene glycol, polyethylene glycol, polypropylene glycol, and glycerin, and polyhydric alcohol derivatives, such as a propylene-based glycol ether; ketones, such as acetone, methyl ethyl ketone, methyl isobutyl ketone, diisobutyl ketone, cyclohexanone, and isophorone; ethers, such as ethyl ether, dioxane, cellosolve, dipropyl ether, and tetrahydrofuran; aliphatic hydrocarbons, such as n-paraffin, naphthene, isoparaffin, kerosene, and mineral oil; aromatic hydrocarbons, such as benzene, toluene, xylene, solvent naphtha, and an alkyl naphthalene; and halogenated hydrocarbons, such as dichloroethane, chloroform, and carbon tetrachloride; esters, such as ethyl acetate, diisopropyl phthalate, dibutyl phthalate, dioctyl phthalate, and dimethyl adipate; lactones, such as γ-butyrolactone; amides, such as dimethylformamide, diethylformamide, dimethylacetamide, and an N-alkylpyrrolidine; nitriles, such as acetonitrile; sulfur compounds, such as dimethyl sulfoxide; plant oils, such as soybean oil, rapeseed oil, cottonseed oil, and castor oil; and water. Those liquid carriers may be used alone or in combination thereof.

The surfactant is not particularly limited, but is preferably a surfactant that gelates in water or shows swellability. Examples thereof include: nonionic surfactants, such as a sorbitan fatty acid ester, a polyoxyethylene sorbitan fatty acid ester, a sucrose fatty acid ester, a polyoxyethylene fatty acid ester, a polyoxyethylene resin acid ester, a polyoxyethylene fatty acid diester, a polyoxyethylene alkyl ether, a polyoxyethylene alkylphenol ether, a polyoxyethylene dialkyl phenyl ether, a polyoxyethylene alkylphenol formalin condensate, a polyoxyethylene polyoxypropylene block polymer, an alkyl polyoxyethylene polypropylene block polymer ether, a polyoxyethylene alkylamine, a polyoxyethylene fatty acid amide, a polyoxyethylene fatty acid bisphenyl ether, a polyalkylene benzyl phenyl ether, a polyoxyalkylene styrene phenyl ether, acetylenediol, a polyoxyalkylene-added acetylenediol, a polyoxyethylene ether-type silicone, an ester-type silicone, a fluorine-based surfactant, polyoxyethylene castor oil, and polyoxyethylene hydrogenated castor oil; anionic surfactants, such as an alkyl sulfate, a polyoxyethylene alkyl ether sulfate, a polyoxyethylene alkyl phenyl ether sulfate, an alkylbenzene sulfonate, a lignosulfonate, an alkyl sulfosuccinate, a naphthalenesulfonate, an alkyl naphthalenesulfonate, a salt of a formalin condensate of naphthalenesulfonic acid, a salt of a formalin condensate of an alkyl naphthalenesulfonic acid, a fatty acid salt, a polycarboxylate, an N-methyl-fatty acid sarcosinate, a resin acid salt, a polyoxyethylene alkyl ether phosphate, and a polyoxyethylene alkyl phenyl ether phosphate; cationic surfactants, for example, alkylamine salts, such as laurylamine hydrochloride, stearylamine hydrochloride, oleylamine hydrochloride, stearylamine acetate, stearylaminopropylamine hydrochloride, an alkyl trimethyl ammonium chloride, and an alkyl dimethyl benzalkonium chloride; and ampholytic surfactants, such as an amino acid-type or betaine-type surfactant. Those surfactants may be used alone or in combination thereof.

In addition, examples of the binder or the tackifier include carboxymethyl cellulose and salts thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of from 6,000 to 20,000, polyethylene oxide having an average molecular weight of from 100,000 to 5,000,000, and natural phospholipids (e.g., cephalic acid and lecithin acid). Those binders or tackifiers may be used alone or in combination thereof.

Examples of the thickener include: water-soluble polymers, such as xanthan gum, guar gum, carboxymethyl cellulose, polyvinylpyrrolidone, a carboxy vinyl polymer, an acrylic polymer, a starch derivative, and a polysaccharide; and inorganic fine powders, such as high-purity bentonite and white carbon. Those thickeners may be used alone or in combination thereof.

Examples of the colorant include: inorganic pigments, such as iron oxide, titanium oxide, and Prussian blue; and organic dyes, such as an alizarin dye, an azo dye, and a metal phthalocyanine dye. Those colorants may be used alone or in combination thereof.

Examples of the extender include a silicone-based surfactant, cellulose powder, dextrin, processed starch, a polyaminocarboxylic acid chelate compound, crosslinked polyvinylpyrrolidone, maleic acid and styrene acid, a methacrylic acid copolymer, a half ester of a polymer of a polyhydric alcohol and a dicarboxylic acid anhydride, and a water-soluble salt of polystyrenesulfonic acid. Those extenders may be used alone or in combination thereof.

Examples of the spreading agent include: various surfactants, such as a sodium dialkyl sulfosuccinate, a polyoxyethylene alkyl ether, a polyoxyethylene alkyl phenyl ether, and a polyoxyethylene fatty acid ester; and paraffin, terpene, a polyamide resin, a polyacrylate, polyoxyethylene, a wax, a polyvinyl alkyl ether, an alkylphenol formalin condensate, and a synthetic resin emulsion. Those spreading agents may be used alone or in combination thereof.

Examples of the antifreezing agent include polyhydric alcohols, such as ethylene glycol, diethylene glycol, propylene glycol, and glycerin. Those antifreezing agents may be used alone or in combination thereof. Examples of the caking inhibitor include polysaccharides, such as starch, alginic acid, mannose, and galactose, and polyvinylpyrrolidone, white carbon, an ester gum, and a petroleum resin. Those caking inhibitors may be used alone or in combination thereof.

Examples of the disintegrant include sodium tripolyphosphate, sodium hexametaphosphate, a stearic acid metal salt, cellulose powder, dextrin, a copolymer of a methacrylic acid ester, polyvinylpyrrolidone, a polyaminocarboxylic acid chelate compound, a sulfonated styrene-isobutylene-maleic acid anhydride copolymer, and a starch-polyacrylonitrile graft copolymer. Those disintegrants may be used alone or in combination thereof.

Examples of the stabilizing agent include: drying agents, such as zeolite, quicklime, and magnesium oxide; antioxidants, such as phenol-based, amine-based, sulfur-based, and phosphoric acid-based antioxidants; and UV absorbers, such as salicylic acid-based and benzophenone-based UV absorbers. Those stabilizing agents may be used alone or in combination thereof.

Examples of the antiseptic agent include potassium sorbate and 1,2-benzothiazolin-3-one. Those antiseptic agents may be used alone or in combination thereof.

The agricultural and horticultural fungicide composition of the present invention can form a multicomponent pest control agent that provides a wider range of agricultural protection by containing, as a combined component, any of components known through, for example, The Pesticide Manual (2013) published by the British Crop Protection Council, the Complete Guide of the Kumiai Agrichemical (2014) published by the National Federation of Agricultural Cooperative Associations, and SHIBUYA INDEX (17th edition) published by the National Agricultural Community Education Association, such as a fungicide, an insecticide, a miticide, a nematicide, a pesticide for snails, an ingestion inhibitor, a herbicide, an algicide, a biopesticide, a pheromone, a natural fungicide, and a natural pesticide. Examples of the combined component are shown below, but the combined component is not limited thereto.

Examples of the fungicide component include iturin A, iturin $A_L$, mycosubtilin, bacillomycin D, bacillomycin F, Bacillomycin Lc, fengycin, plipastatin, fusaricidin, bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metoconazole, myclobutanil, penconazole, propiconazole, prothioconazole, cimeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole, oxpoconazole fumarate, hymexazol, azoxystrobin, dimoxystrobin, enestroburin, fluoxastrobin, kresoxim-methyl, metominostrobin, orysastrobin, picoxystrobin, pyraclostrobin, trifloxystrobin, carboxin, benalaxyl, boscalid, bixafen, fenhexamid, flutolanil, furametpyr, mepronil, metalaxyl, mefenoxam, ofurace, oxadixyl, oxycarboxin, penthiopyrad, thifluzamide, tiadinil, dimethomorph, flumorph, flumetover, fluopicolide, carpropamid, diclocymet, mandipropamid, fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, anilazine, diclomezine, pyroquilon, proquinazid, tricyclazole, captafol, captan, dazomet, folpet, fenoxanil, quinoxyfen, amisulbrom, manzeb, maneb, metam, metiram, ferbam, propineb, thiuram, zineb, ziram, diethofencarb, iprovalicarb, benthiavalicarb-isopropyl, propamocarb hydrochloride, thiophanate-methyl, pyribencarb, Bordeaux mixture, basic copper chloride, basic copper sulfate, cupric hydroxide, copper 8-hydroxyquinoline, dodine, iminoctadine albesilate, iminoctadine acetate, guazatine, kasugamycin, streptomycin, polyoxin, oxytetracycline, validamycin A, binapacryl, dinocap, dinobuton, dithianon, isoprothiolane, edifenphos, iprobenfos, fosetyl, fosetyl-aluminum, pyrazophos, tolclofos-methyl, chlorothalonil, dichlofluanid, flusulfamide, hexachlorobenzene, phthalide, pencycuron, quintozene, cyflufenamid, cymoxanil, dimethirimol, ethirimol, furalaxyl, metrafenone, spiroxamine, amobam, sulfur, lime sulfur, echlomezole, potassium hydrogen carbonate, calcium hydrogen carbonate, thiadiazine, tecloftalam, triazine, copper nonylphenol sulfonate, hydroxyisoxazole, fluoroimide, polycarbamate, methasulfocarb, EDDP, IBP, TPN, tolfenpyrad, fluopyram, isotianil, oxathiapiprolin, and isopyrazam.

Examples of the insecticide, the miticide, the nematicide, the pesticide for snails, and the ingestion inhibitor include 1,2-dichloropropane, 1,3-dichloropropene, abamectin, acephate, acequinocyl, acetamiprid, acethion, acetophos, acetoprole, acrinathrin, acrylonitrile, afidopyropen, alanycarb, aldoxycarb, allethrin, allicin, allosamidin, allyxycarb, α-cypermethrin, α-endosulfan, amidithion, amidoflumet, aminocarb, amitone, amitraz, anabasine, aramite, athidathion, azadirachtin, azamethiphos, azinephos-ethyl, azinephos-methyl, azobenzene, azocyclotin, azothoate, barium hexafluorosilicate, barthrin, benclothiaz, bendiocarb, benfuracarb, benoxafos, bensultap, benzoximate, benzyl benzoate, β-cyfluthrin, β-cypermethrin, bifenazate, bifenthrin, bifujunzhi, binapacryl, bioallethrin, bioethanomethrin, biopermethrin, bistrifluron, borax, boric acid, brofenvalerate, broflanilide, brofluthrinate, bromethrin, bromfenvinphos, bromoacetamide, bromocyclene, bromo-DDT, bromophos, bromophos-ethyl, bromopropylate, bufencarb, buprofezin, butacarb, butathiofos, butethrin, butocarboxim, butonate, butoxy-carboxim, cadusafos, calcium polysulfate, calvinphos, camphechlor, carbanolate, carbanyl, carbofuran, carbon disulfide, carbon tetrachloride, carbonyl sulfide, carbophenothion, carbosulfan, cartap, carvacrol, quinomethionate, chloramine phosphorus, chlorantraniliprole, chlorbenside, chlorbenzuron, chlorbicyclene, chlordecone, chlorempenthrin, chlorethoxyfos, chlorfenapyr, chlorfenethol, chlorfenson, chlorfensulfide, chlorfenvinphos, chlorfluazuron, chlormephos, chloroform, chloromebuform, chloromethiuron, chloropicrin, chloroprallethrin, chloropropylate, chlorphoxim, chlorprazophos, chlorpyrifos, chlorpyrifos-methyl, chlorthiophos, chromafenozide, cinerin I, cinerin II, a cinerin complex, cismethrin, clenpyrin, cloethocarb, clofentezine, closantel, clothianidin, colophonate, copper naphthenate, copper oleate, copper sulfate, coumaphos, coumithoate, CPMC, crotamiton, crotoxyphos, crufomate, cryolite, cyanofenphos, cyanogen, cyanophos, cyanthoate, cyantraniliprole, cyclaniliprole, cyclethrin, cycloprate, cycloprothrin, cyenopyrafen, cyflumetofen, cyfluthrin, cyhalodiamide, cyhalothrin, cyhexatin, cymiazole, cypermethrin, cyromazine, cythioate, dayoutong, dazomet, DBCP, DCIP, decarbofuran, deltamethrin, demephion, demephion-O, demephion-S, demeton, demeton-methyl, demeton-O, demeton-O-methyl, demeton-S, demeton-S-methyl, demeton-S-methyl sulfone, d-fanshiluquebingjuzhi, diafenthiuron, dialifos, diamidafos, diatomaceous earth, diazinon, dicapthon, dichlofenthion, dichlofluanid, dichlorbenzuron, dichlorvos, dicloromezothiaz, dicofol, dicresyl, dicrotophos, dicyclanil, dienochlor, diflovidazin, diflubenzuron, dilor, dimefluthrin, dimefox, dimethane, dimethacarb, dimethoate, dimethrin, dimethylvinphos, dimethylan, dinex, dinobuton, dinocap, dinocap-4, dinocap-6, dinocton, dinopenton, dinoprop, dinosam, dinosulfon, dinotefuran, dinoterbon, diofenolan, dioxabenzofos, dioxacarb, dioxathion, diphenyl sulfone, dipymetitrone, disulfiram, disulfoton, dithiocrofos, dithioether, d-limonene, DNOC, dofenapyn, doramectin, ecdysterone, emamectin, EMPC, empenthrin, endothion, endoline, EPN, epofenonate, eprinomectin, ε-metofluthrin, ε-momfluorothrin, esdepallethrin, esfenvalerate, etaphos, ethiofencarb, ethion, ethiprole, ethoate-methyl, ethoprophos, ethyl fumarate, ethyl-DDD, ethylene dibromide, ethylene dichloride, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpyrithrin, fenpropathrin, fenpyroximate, fenson, fensulfothion, fenthion, fenthion-ethyl, fentrifanil, fenvalerate, ferric phosphate, fipronil, flometoquin, flonicamid, fluacrypyrim, fluazaindolizine, fluazuron, flubendiamide, flubenzimine, flucofuron, flucycloxuron, flucythrinate, fluenethyl, fluensulfone, flufenerim, flufenoxuron, flufenoxystrobin, flufenprox, flufiprole, fluhexafon, flumethrin, fluorbenside, flupyradifurone, fluralaner, flusulfamide, fluvalinate, fluxametamide, fonofos, formetanate, formetanate hydrochloride, formothion, formparanate, phosmethylan, fospirate, fosthiazate, fosthietan, furamethrin, furan tebufenozide, furanthiocarb, furethrin, furfural, γ-cyhalothrin, γ-HCH, genite, guazatine, halfenprox, halofenozide, HCH, HEOD, heptafluthrin, heptenophos, heterophos, hexachlorophene, hexaflumuron, hexythiazox, HHDN, hydramethylnon, hydroprene, hyquincarb, imicyafos, imidacloprid, imidaclothiz, imiprothrin, indoxacarb, IPSP, isamidofos, isazophos, isobenzan, isocarbophos, isodrin, isofenphos, isofenphos-methyl, isolan, isoprocarb, isoprothiolane, isothioate, isoxathion, ivermectin, japothrins, jasmolin I, jasmolin II, jiahuangchongzong, iodofenphos, juvenile hormone I, juvenile hormone II, juvenile hormone III, kadethrin, κ-bifenthrin, κ-tefluthrin, kelevan, quinoprene, λ-cyhalothrin, lepimectin, leptophos, lirimfos, lufenuron, lythidathion, malathion, malonoben, maltodextrin, matrine, mazidox, mecarbam, mecarphon, medimeform, menazon, meperfluthrin, mephosfolan, mesulfen, mesulfenphos, metaflumizone, metaldehyde, metam, metacrifos, methidathion, methiocarb, methocrotophos, methomyl, methoprene, methothrin, methoxychlor, methoxyfenozide, methyl iodide, methyl isothiocyanate, methylacetophos, methyl chloroform, methylene chloride, metofluthrin, metolcarb, metoxadiazone, mevinphos, mexacarbate, milbemectin, milbemycin oxime, mipafox, mirex, MNAF, momfluorothrin, morphothion, moxidectin, naphthalophos, naled, naphthalene, niclosamide, nicotine, nifluridide, a nikkomycin complex, nitenpyram, nithiazine, nitrilacarb, nornicotine, novaluron, noviflumuron, omethoate, oxamyl, oxydemeton-methyl, oxydeprofos, oxydisulfoton, oxymatrine, paichongding, paradichlorobenzene, penfluron, pentachlorophenol, pentmethrin, permethrin, phenkapton, phenothrin, phenproxide, phenthoate, phorate, phosalone, phosphorane, methylphosphorane, phosglycin, phosmet, phosnichlor, phosphine, phosphocarb, phostin, phoxim, phoxim-methyl, pirimetaphos, pirimicarb, pirimioxyphos, pirimiphos-ethyl, pirimiphos-methyl, plifenate, polythialan, potassium thiocyanate, prallethrin, precocene I, precocene II, precocene III, primidophos, proclonol, profenofos, profluthrin, promacyl, promecarb, propaphos, propargite, propathrin, propetamphos, propoxur, prothidathion, prothiofos, prothoate, protrifenbute, pyflubumide, pymetrozine, pyraclofos, pyrafluprole, pyramat, pyrazophos, pyrazothion, pyresmethrin, pyrethrin I, pyrethrin II, pyrethrin, pyridab en, pyridalyl, pyridafenthion, pyrifluquinazon, pyrimidifen, pyriminostrobin, piriminate, pyriprole, pyriproxyfen, pyrolan, quassia, quinalphos, quinalphos-methyl, quinothion, quintiofos, rafoxanide, resmethrin, rhodojaponin III, rotenone, ryania, sabadilla, sanguinarine, schradan, selamectin, semiamitraz, semiamitraz chloride, silafluofen, silica gel, sodium fluoride, sodium hexafluorosilicate, sodium chlorophenol, sodium tetrathiocarbonate, sodium thiocyanate, sophamide, spinetoram, spinosad, spirodiclofen, spiromesifen, spirotetramat, sulcofuron, sulcofuron sodium salt, sulfiram, sulfluramid, sulfotep, sulfoxaflor, sulfoxime, sulfur, sulfuryl fluoride, sulprofos, τ-fluvalinate, tazimcarb, TDE, tebufenozide, tebufenpyrad, tebupirimphos, teflubenzuron, tefluthrin, temephos, TEPP, terallethrin, terbufos, tetrachloroethane, tetrachlorovinphos, tetradifon, tetramethrin, tetramethylfluthrin, tetranactin, tetraniliprole, tetrasul, tetracypermethrin, thiacloprid, thiamethoxam, thiapronil, triclofos, thiocarboxime, thiocyclam, thiodicarb, thiofanox, thiofluoximate, thiometon, thionazin, thioquinox, thiosultap, thiosultap sodium salt, tioxazafen, tirpate, tolfenpyrad, tralocythrin, tralomethrin, tralopyril, trans-permethrin, triarathene, triazamate, triazophos, trichlorfon, trichlormetaphos-3, trichloronat, trifenmorph, trifenofos, triflumezopyrim, triflumuron, trimethacarb, triprene, triptolide, valerate, vamidothion, vaniliprole, xiaochongliulin, XMC, xylenols, xylylcarb, yishijing, ζ-cypermethrin, zolaprofos, α-ecdysone, AKD-1193, DKN-2601, IKI-3106, KUI-1103, KUI-1301, KYIF-1402, ME5382, MIE-1209, MIE-1405, MSI-1301, MSI-1302, NA-89, NC-515, ZDI-2501, and ZDI-2502.

Examples of the herbicide and the algicide include 2,3,6-TBA, 2,4,5-TB, 2,4-D, 2,4-DB, 2,4-DEB, 2,4-DEP, 3,4-DA, 3,4-DB, 3,4-DP, 4-CPA, 4-CPB, 4-CPP, acetochlor, acifluorfen, aclonifen, acrolein, allidochlor, alloxydim, allyl alcohol, alorac, amethydione, ametrine, amibuzin, amicarbazone, amidosulfuron, aminocyclopyrachlor, aminopyralid, amiprophos-methyl, amiprophos, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, bentranil, benzadox, benzalkonium chloride, benzfendizone, benzipram, benzobicyclon, benzofenap, benzofluor, benzoylprop, benzthiazuron, bethoxazin, bicyclopyrone, bifenox, bialaphos, bispyribac, borax, bromacil, bromobonil, bromobutide, bromofenoxim, bromoxynil, brompyrazon, butachlor, butafenacil, butamiphos, butenachlor, bithiazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, CDEA, CEPC, chlomethoxynil, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornidine, chlornitrofen, chloropon, chlortoluron, chloroxuron, chloroxynil, chlorprocarb, chlorpropham, chlorsulfuron, chlorthal, chlorthiamid, cinidon-ethyl, cinmethylin, cinosulfuron, cisanilide, clacyfos, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanamide, cyanatryn, cyanazine, cyanogen, cybutryne, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichlone, dichloralurea, dichromate, dichlorophene, dichlorprop, dichlorprop-P, diclofop, diclosulam, diethamquat, diethatyl-ethyl, difenopentene, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoterb, diphenamid, dipropalin, dipropetryn, diquat, disul, dithioether, dithiopyr, diuron, DMPA, DNOC, DSMA, EBEP, eglinazine, endothall, epronaz, EPTC, erbon, erlujixiancaoan, esprocarb, ethachlor, ethalfluralin, ethametsulfuron, ethaprochlor, ethidimuron, ethiolate, ethiozin, ethofumesate, ethoxyfen, ethoxysulfuron, ethinofen, etnipromid, etobenzanid, EXD, fenasulam, fenoprop, fenoxaprop, fenoxaprop-P, fenoxasulfone, fenquinotrione, fenteracol, fenthiaprop, tin, fentrazamide, fenuron, iron sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamin, fucaojing, fucaomi, funaihecaoling, furyloxyfen, glufosinate, glufosinate-P, glyphosate, halauxifen, halosafen, halosulfuron, haloxydine, haloxyfop, haloxyfop-P, herbimycin, hexachloroacetone, hexaflurate, hexazinone, huancaiwo, huangcaoling, hydrated lime, imazamethabenz, imazamox, imazapic, imazapyr, imazaquin, imazethapyr, imazosulfuron, indanofan, indaziflam, iodobonil, iodosulfuron methyl, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, kuicaoxi, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiopyrisulfuron, methiozolin, methiuron, methometon, methoprotryne, methoxyphenone, methyl bromide, methyl iodide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monosulfuron, monuron, morfamquat, MSMA, nabam, naproanilide, napropamide-M, naptalam, neburon, nicosulfuron, nipyraclofen, nitralin, nitrofen, nitrofluorfen, norflurazon, noruron, OCH, orbencarb, o-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenyl laurate, pentanochlor, pentoxazone, perfluidone, pethoxamid, phenisopham, phenmedipham, phenmedipham-ethyl, phenobenzuron, picloram, picolinafen, pinoxaden, piperophos, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolate, pyrazosulfuron, pyrazoxyfen, pyribambenz-isopropyl, pyribambenz-propyl, pyribenzoxim, pyribencarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, sebuthylazine, secbumeton, sethoxydim, shuangjiaancaolin, siduron, simazine, simeton, simetryn, SMA, S-metolachlor, sodium chlorate, sulcotrione, sulfallate, sulfentrazone, sulfometuron, sulfosulfuron, sulglycapin, swep, tavron, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, triaziflam, thiazopyr, thidiazimin, thidiazuron, thiencarbazone, thifensulfuron, thiobencarb, tiafenacil, tiocarbazil, tioclorim, tolpyralate, topramezone, tralkoxydim, triafamone, triallate, triasulfuron, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor, zuomihuanglong, DAH-500, and SL-261.

Examples of the biopesticide include Nuclear polyhedrosis virus (NPV), Granulosis virus (GV), Cytoplasmic polyhedrosis virus (CPV), *Steinernema carpocapsae, Steinernema glaseri, Monacrosporium phymatophagum, Steinernema kushidai, Pasteuria penetrans, Agrobacterium radiobacter, Bacillus subtilis, Bacillus amyloliquefaciens, Bacillus cereus, Bacillus pumilus, Bacillus licheniformis, Bacillus mycoides, Bacillus methylotrophycus, Bacillus simplex, Bacillus firmus, Bacillus megaterium, Bacillus coagulans, Bacillus oryzicola, Bacillus* sp., *Bacillus thuringiensis, Erwinia carotovora, Pseudomonas fluorescens, Pseudomonas cepacia, Pseudomonas putida, Talaromyces flavus, Trichoderma atroviride, Beauveria brongniartii, Beauveria bassiana, Paecilomyces fumosoroseus, Verticillium lecanii, Xanthomonas campestris, Encarsia formosa, Eretmocerus eremicus, Eretmocerus mundus, Aphidoletes colemania, Aphidoletes aphidimyza, Diglyphus isaea, Dacnusa sibirica, Phytoseiulus persimilis, Amblyseius cucumeris, Amblyseius californicus,* and *Orius strigicollis.*

Examples of the pheromone (pest attractant) include brevicomin, ceralure, codlelure, cue-lure, disparlure, dominicalure-1, eugenol, frontalin, gossyplure, grandlure, hexalure, ipsdienol, ipsenol, japonilure, latilure, lineatin, litlure, looplure, medlure, megatomoic acid, methyl eugenol, moguchun, muscalure, orfralure, oryctalure, ostramone, rescalure, siglure, sulcatol, trimedlure, trunc-call, and α-multistriatin.

Examples of the pheromone (pest repellent) include acrep, butopyronoxyl, camphor, d-camphor, carboximide, dibutyl phthalate, diethyltoluamide, dimethyl carbate, dimethyl phthalate, dibutyl succinate, ethohexadiol, hexamide, icaridin, methoquin-butyl, methylneodecanamide, 2-(methylthio)ethanol, oxamate, quwenzhi, quyingding, rebemide, and zengxiaoan.

Examples of the natural fungicide and the natural pesticide include machine oils, methylphenyl acetate, α-pinene, protein hydrolysates, (Z)-1-Tetradecen-1-ol, and turpentine.

The fungicide composition according to the present invention can also form a multicomponent pest control agent that provides a wider range of agricultural protection by containing, as a combined component, at least one kind of biologically active component, for example, a plant growth regulator, such as a root stimulator, or a fertilizer, such as a plant nutrient, as required.

A plant disease controlling method of the present invention includes a step of treating a plant or a plant peripheral region with the agricultural and horticultural fungicide composition of the present invention. Herein, the plant refers to a plant or a group of plants, such as a wild plant, a grown plant, a naturally occurring plant, and a cultivated plant, and also encompasses plants created by a breeding method such as an introduction breeding method, a breeding-by-separation method, a crossbreeding method, a heterosis breeding method, a mutation breeding method, a polyploid breeding method, a gene recombination (gene introduction) method, or marker-assisted selection. In addition, the plant to be treated may be any of the whole of the plant and part of the plant. Further, the plant peripheral region refers to a soil (soil to be seeded with seeds), a paddy field, water for hydroponics, a cultivation material, or the like. In addition, the treatment of the plant or the plant peripheral region refers to misting, spreading, spreading as powder, spraying, dispersing, soaking, drenching, inserting, sprinkling (exposing to water), bubbling, depositing, dressing, coating, blowing, fumigating, smoking, hazing, painting, or the like.

When treatment is performed with the fungicide composition according to the present invention in order to control phytopathogenic microorganisms or a plant disease caused thereby, the treatment may be performed throughout the breeding period and storage period of the plant irrespective of whether the treatment is performed before or after infection by the phytopathogenic microorganisms. Herein, part of the plant means all parts constituting the plant including the leaf, stem, trunk, branch, flower, fruiting body, fruit, seed, root, tuber, and rhizome of the plant, or a combination thereof.

In order to control the phytopathogenic microorganisms and the plant disease caused thereby, the agricultural and horticultural fungicide composition according to the present invention may be used with its treatment amount being adjusted to an effective but non-phytotoxic amount. Herein, the effective but non-phytotoxic amount is an amount that allows sufficient control of the phytopathogenic microorganisms or the plant disease caused thereby and does not harm the plant, and this amount may vary in a relatively wide range depending on the microorganisms to be controlled, the plant to which the composition is applied, the natural environment of use, and the components of the composition according to the present invention.

A further aspect of the present invention relates to a seed treated with the agricultural and horticultural fungicide composition according to the present invention. The seed is used for preventing the occurrence of a plant disease caused by phytopathogenic microorganisms. When a seed infected with or having attached thereto phytopathogenic microorganisms (hereinafter referred to as contaminated seed) contaminates healthy seeds, the contaminated seed serves as an infection source of the phytopathogenic microorganisms to transmit the disease to healthy plants that are grown nearby. Therefore, the seed treated with the fungicide composition according to the present invention having high fungicide activity on plant disease microorganisms serves as effective means for preventing the occurrence of a plant disease and the transmission of pathogenic microorganisms to healthy plants.

The agricultural and horticultural fungicide composition according to the present invention may be used for seeds of all plants. The seed according to the present invention is effective as means for preventing the occurrence of a plant disease caused by phytopathogenic microorganisms particularly in rice, wheat, barley, rye, corn, soybeans, cotton, potato, sugar beet, and the like, which are cultivated in a large scale and hence are liable to suffer wider damage from the transmission of the disease due to the contaminated seed. In addition, treatment of a seed of a genetically modified crop with the fungicide composition according to the present invention is also effective as means for preventing the occurrence of a plant disease caused by phytopathogenic microorganisms.

EXAMPLES

The present invention is specifically described below by way of Production Examples, Formulation Examples (Prescription Examples), and Test Examples. However, the present invention is not limited to these Examples.

Prumycin used in the following Test Examples was prepared in Production Example 1, [Ile$^7$]surfactin was prepared in Production Example 2, and surfactin (derived from *Bacillus subtilis*, mixture containing C13 to C15 β-OH fatty acids) was obtained from Sigma-Aldrich Japan.

Production Example 1

Synthesis of Prumycin

Prumycin was synthesized in accordance with the method of Iwabuchi et al. (J. Carbohydr. Chem. 1988, 7, 605-616). That is, D-arabinose (25 g) was converted to 4-azido-2-(benzyloxycarbonyl)amino-2,4-dideoxy-α-$_L$-arabinopyranoside by 1-O-benzylation, 3,4-O-isopropylidene acetal protection, 2-benzoylation, isopropylidene acetal deprotection, 4-selective azide substitution, benzoyl deprotection, epoxidation, ring-opening amination, and N-Cbz protection (9.6 g, 9 steps, 14% yield). Azide selective reduction, condensation with N-carbobenzoxy-D-alanine (N-Cbz-$_D$-alanine), and reductive deprotection of the intermediate (984 mg) gave prumycin hydrochloride (424 mg, 4 steps, 59% yield).

Production Example 2

Production of [Ile$^7$]Surfactin

A *Bacillus* sp. strain AT-332 was inoculated to a 5,000 ml jar fermentor containing 2,000 ml of LB medium (peptone: 20 g, yeast extract: 10 g, sodium chloride: 20 g, water: balance), and was then, as main culture, cultured at 35° C. for 3 days under the conditions of a number of revolutions of 500 rpm and an aeration rate of 1 L/h.

About 1,800 g of the culture obtained by the main culture was centrifuged to provide 1,500 ml of a culture supernatant. 1,500 g of the resultant culture supernatant was adjusted to a pH of 4.0 with HCl, and extracted three times with an equal amount of ethyl acetate. The ethyl acetate fraction was concentrated, suspended in water, and then adjusted to a pH of 7.0 with sodium hydroxide. The resultant solution was adsorbed to Sep-Pak (trademark) C18 (manufactured by Waters), which had been equilibrated with water in advance, and was eluted with 80% acetonitrile. The resultant fraction was subjected to HPLC, and a main peak was isolated (50 mg). NMR analysis identified the peak as iso-C14 [Ile$^7$] surfactin.

Formulation Example 1

Preparation of Prumycin Hydrochloride Wettable Powder and Surfactin Family Member Wettable Powder 5 Parts (parts by mass, the same applies hereinafter) each of prumycin hydrochloride obtained in Production Example 1, commercially available surfactin, and iso-C14 [Ile$^7$] surfactin obtained in Production Example 2, 50 parts of diatomaceous earth, 35 parts of white carbon, 8 parts of sodium lignosulfonate, and 2 parts of sodium alkylnaphthalenesulfonate were mixed and pulverized to provide respective wettable powders. As a control, Daconil 1000 (manufactured by SDS Biotech K.K.: active component TPN 40%) was purchased and tested.

Formulation Example 2

Preparation of Wettable Powder Containing Prumycin Hydrochloride and Surfactin Family Member 5 Parts of prumycin hydrochloride obtained in Production Example 1, 5 parts of commercially available surfactin, 50 parts of diatomaceous earth, 30 parts of white carbon, 8 parts of sodium lignosulfonate, and 2 parts of sodium alkylnaphthalenesulfonate were mixed and pulverized to provide a wettable powder containing prumycin hydrochloride and commercially available surfactin. In addition, 5 parts of prumycin hydrochloride obtained in Production Example 1, 5 parts of iso-C14 [Ile$^7$]surfactin obtained in Production Example 2, 50 parts of diatomaceous earth, 30 parts of white carbon, 8 parts of sodium lignosulfonate, and 2 parts of sodium alkylnaphthalenesulfonate were mixed and pulverized to provide a wettable powder containing prumycin hydrochloride and iso-C14 [Ile$^7$]surfactin.

Test Example 1

Effect Test on Cucumber Gray Mold

Cotyledons were harvested from cucumbers (variety: Hikari No. 3 P-type) that had been grown in a greenhouse for 3 weeks in a plastic pot having a diameter of 6 cm. The harvested cotyledons were placed side by side in a Tupperware container in which wetted filter paper was laid, and a paper disc having a diameter of 8 mm was placed on the center of each of the cotyledons. To each paper disc, 50 µL of a suspension of *Botrytis cinerea* spores ($2\times10^4$/ml, containing 2% of sucrose and 0.2% of a yeast extract) was added, and at the same time, 50 µL of a phosphate buffer (40 mM, pH 7.2) having dissolved therein each wettable powder prepared in Formulation Example 1 at a target concentration was added. A lid was placed on the Tupperware container, which was kept at 20° C. for 4 days. After that, diseased areas were investigated with eyes to determine a preventive value. The preventive value (%) was calculated using the following equation. The results are shown in Table 2.

Preventive value=(1−(diameter of infection zone in leaf with test compound/diameter of infection zone in control leaf))×100

TABLE 2

| Added chemical | Preventive value (%) |
|---|---|
| Prumycin 10 ppm | 100 |
| Prumycin 5 ppm | 95 |
| Prumycin 2 ppm | 55 |
| Prumycin 1 ppm | 45 |
| Prumycin 0.5 ppm | 6 |
| — + Surfactin 10 ppm | 0 |
| — + Surfactin 1 ppm | 0 |
| — + [Ile$^7$]Surfactin 10 ppm | 0 |
| — + [Ile$^7$]Surfactin 1 ppm | 0 |
| Prumycin 10 ppm + Surfactin 10 ppm | 100 |
| Prumycin 5 ppm + Surfactin 10 ppm | 100 |
| Prumycin 2 ppm + Surfactin 10 ppm | 100 |
| Prumycin 1 ppm + Surfactin 10 ppm | 100 |
| Prumycin 0.5 ppm + Surfactin 10 ppm | 91 |
| Prumycin 10 ppm + Surfactin 1 ppm | 100 |
| Prumycin 5 ppm + Surfactin 1 ppm | 100 |
| Prumycin 2 ppm + Surfactin 1 ppm | 100 |
| Prumycin 1 ppm + Surfactin 1 ppm | 98 |
| Prumycin 0.5 ppm + Surfactin 1 ppm | 57 |
| Prumycin 10 ppm + [Ile$^7$]Surfactin 10 ppm | 100 |
| Prumycin 5 ppm + [Ile$^7$]Surfactin 10 ppm | 100 |
| Prumycin 2 ppm + [Ile$^7$]Surfactin 10 ppm | 100 |
| Prumycin 1 ppm + [Ile$^7$]Surfactin 10 ppm | 100 |
| Prumycin 0.5 ppm + [Ile$^7$]Surfactin 10 ppm | 96 |
| Prumycin 10 ppm + [Ile$^7$]Surfactin 1 ppm | 100 |
| Prumycin 5 ppm + [Ile$^7$]Surfactin 1 ppm | 100 |
| Prumycin 2 ppm + [Ile$^7$]Surfactin 1 ppm | 100 |
| Prumycin 1 ppm + [Ile$^7$]Surfactin 1 ppm | 99 |
| Prumycin 0.5 ppm + [Ile$^7$]Surfactin 1 ppm | 62 |
| TPN 10 ppm | 100 |
| TPN 5 ppm | 100 |
| TPN 2 ppm | 66 |
| TPN 1 ppm | 54 |
| TPN 0.5 ppm | 21 |

TPN: commercially available agricultural chemical Daconil 1000

No effect was found in 1 ppm to 10 ppm of each surfactin family member itself. However, as compared to the case of treatment with prumycin alone, the preventive value was clearly enhanced by adding the surfactin family member (1 ppm or more) to prumycin (0.5 ppm or more), revealing the effectiveness of the present invention. The section tested with prumycin alone already included generally used surfactants, such as sodium lignosulfonate and sodium alkylnaphthalenesulfonate, as shown in Formulation Example, but when the surfactin family member was added thereto, a clear effect was found. This is the exhibition of a unique synergistic effect of prumycin and the surfactin family member. In addition, the effect was superior to that of the commercially available agricultural chemical TPN (Daconil 1000), and was extremely promising.

Test Example 2

Effect Test on Cucumber Powdery Mildew

A sufficient amount of a dilute solution of each wettable powder prepared in Formulation Example 1 was spread with a spray gun on cucumbers (variety: Hikari No. 3 P-type) that had been grown in a greenhouse to the third-leaf unfolding stage in a plastic pot having a diameter of 6 cm. The next day, the cucumbers were inoculated with a suspension of cucumber powdery mildew spores by misting. The cucumbers were allowed to stand in the greenhouse for 10 days, and diseased area ratios in the first leaf and the second leaf (first and second leaves from the ground) were investigated with eyes to determine a preventive value. The preventive value (%) was calculated using the following equation. The results are shown in Table 3.

Preventive value=(1−(ratio of infection zone in leaf with test compound/ratio of infection zone in control leaf))×100

TABLE 3

| Added chemical | Preventive value (%) |
|---|---|
| Prumycin 10 ppm | 95 |
| Prumycin 5 ppm | 69 |
| Prumycin 2 ppm | 44 |
| Prumycin 1 ppm | 21 |
| Prumycin 0.5 ppm | 7 |
| — + Surfactin 10 ppm | 0 |
| — + Surfactin 1 ppm | 0 |
| — + [Ile$^7$]Surfactin 10 ppm | 0 |
| — + [Ile$^7$]Surfactin 1 ppm | 0 |
| Prumycin 10 ppm + Surfactin 10 ppm | 100 |
| Prumycin 5 ppm + Surfactin 10 ppm | 98 |
| Prumycin 2 ppm + Surfactin 10 ppm | 75 |
| Prumycin 1 ppm + Surfactin 10 ppm | 74 |
| Prumycin 0.5 ppm + Surfactin 10 ppm | 44 |
| Prumycin 10 ppm + Surfactin 1 ppm | 100 |
| Prumycin 5 ppm + Surfactin 1 ppm | 91 |
| Prumycin 2 ppm + Surfactin 1 ppm | 87 |
| Prumycin 1 ppm + Surfactin 1 ppm | 45 |
| Prumycin 0.5 ppm + Surfactin 1 ppm | 41 |
| Prumycin 10 ppm + [Ile$^7$]Surfactin 10 ppm | 100 |
| Prumycin 5 ppm + [Ile$^7$]Surfactin 10 ppm | 99 |
| Prumycin 2 ppm + [Ile$^7$]Surfactin 10 ppm | 61 |
| Prumycin 1 ppm + [Ile$^7$]Surfactin 10 ppm | 66 |
| Prumycin 0.5 ppm + [Ile$^7$]Surfactin 10 ppm | 35 |
| Prumycin 10 ppm + [Ile$^7$]Surfactin 1 ppm | 100 |
| Prumycin 5 ppm + [Ile$^7$]Surfactin 1 ppm | 88 |
| Prumycin 2 ppm + [Ile$^7$]Surfactin 1 ppm | 66 |

TABLE 3-continued

| Added chemical | Preventive value (%) |
|---|---|
| Prumycin 1 ppm + [Ile$^7$]Surfactin 1 ppm | 52 |
| Prumycin 0.5 ppm + [Ile$^7$]Surfactin 1 ppm | 47 |
| TPN 10 ppm | 100 |
| TPN 5 ppm | 81 |
| TPN 2 ppm | 55 |
| TPN 1 ppm | 35 |
| TPN 0.5 ppm | 15 |

TPN: commercially available agricultural chemical Daconil

No effect was found in 1 ppm to 10 ppm of each surfactin family member itself. However, when prumycin and the surfactin family member according to the present invention were combined, the diseased ratio of cucumber powdery mildew was markedly reduced as compared to the non-treated section, indicating that an extremely high controlling effect was obtained. The section tested with prumycin alone already included generally used surfactants, such as sodium lignosulfonate and sodium alkylnaphthalenesulfonate, as shown in Formulation Example, but when the surfactin family member was added thereto, a clear effect was found. This is the exhibition of a unique synergistic effect of prumycin and the surfactin family member. In addition, the effect was superior to that of the commercially available agricultural chemical TPN (Daconil 1000), and was extremely promising.

Test Example 3

Storage Stability Test

Each wettable powder containing prumycin hydrochloride and a surfactin family member prepared in Formulation Example 2 was mixed with each of 1 mass % and 5 mass % of calcium chloride, and the mixture was subjected to heat treatment under sealing at 54° C. for 2 weeks. An effect test on cucumber powdery mildew was performed using the wettable powder subjected to the heat treatment and the wettable powder not subjected thereto, by the same method as in Test Example 2. The results are shown in Table 4.

TABLE 4

| Added chemical | Calcium chloride concentration | Treatment at 54° C. for 2 weeks | Preventive value (%) |
|---|---|---|---|
| Prumycin 10 ppm + Surfactin 10 ppm | 0% | Absent | 100 |
| Prumycin 10 ppm + Surfactin 10 ppm | 0% | Present | 21 |
| Prumycin 10 ppm + Surfactin 10 ppm | 1% | Absent | 99 |
| Prumycin 10 ppm + Surfactin 10 ppm | 1% | Present | 79 |
| Prumycin 10 ppm + Surfactin 10 ppm | 5% | Absent | 100 |
| Prumycin 10 ppm + Surfactin 10 ppm | 5% | Present | 98 |
| Prumycin 10 ppm + Surfactin 10 ppm | 5% (calcium carbonate) | Absent | 99 |
| Prumycin 10 ppm + Surfactin 10 ppm | 5% (calcium carbonate) | Present | 24 |
| Prumycin 10 ppm + [Ile$^7$]Surfactin 10 ppm | 0% | Absent | 99 |
| Prumycin 10 ppm + [Ile$^7$]Surfactin 10 ppm | 0% | Present | 15 |
| Prumycin 10 ppm + [Ile$^7$]Surfactin 10 ppm | 1% | Absent | 98 |
| Prumycin 10 ppm + [Ile$^7$]Surfactin 10 ppm | 1% | Present | 85 |
| Prumycin 10 ppm + [Ile$^7$]Surfactin 10 ppm | 5% | Absent | 99 |
| Prumycin 10 ppm + [Ile$^7$]Surfactin 10 ppm | 5% | Present | 99 |

Without the addition of calcium chloride, the activity of the wettable powder was extremely lowered by the heat treatment, but its effect was remarkably enhanced by incorporating 1 mass % or 5 mass % of calcium chloride. The stabilizing effect of calcium chloride was found on both the wettable powder of prumycin and surfactin, and the wettable powder of prumycin and [Ile$^7$]surfactin. Meanwhile, a stabilizing effect was not found in the addition of calcium carbonate. It is said that heat treatment at 54° C. for 2 weeks is thermodynamically equivalent to a thermal history of 2 years at room temperature. Thus, it was confirmed that the composition containing the surfactin family member and calcium chloride in addition to prumycin was an agricultural and horticultural composition excellent in effect and also excellent in storage stability.

INDUSTRIAL APPLICABILITY

The composition containing prumycin and the surfactin family member as active components of the present invention has excellent fungicide activity, is enhanced in storage stability when further containing calcium chloride, and can be used as an agricultural and horticultural fungicide composition having a high effect and being excellent in stability.

The invention claimed is:

1. An agricultural and a horticultural fungicide composition, comprising a synergistically effective amount of prumycin and a surfactin family member as active components.

2. The agricultural and horticultural fungicide composition according to claim 1, in which the surfactin family member comprises surfactin and/or [Ile$^7$]surfactin.

3. The agricultural and horticultural fungicide composition according to claim 1, further comprises 0.1 mass % to 10 mass % of calcium chloride.

4. A plant disease controlling method, which comprises applying to a plant the agricultural and horticultural fungicide composition of claim 1.

5. The plant disease controlling method according to claim 4, in which a concentration of prumycin in a liquid to be applied at a time of the applying to a plant is 0.5 ppm or more.

6. The plant disease controlling method according to claim 4, in which a concentration of the surfactin family member in a liquid to be applied at a time of the applying to a plant is 1 ppm or more.

* * * * *